United States Patent [19]

Kasahara et al.

[11] 3,971,848

[45] July 27, 1976

[54] LUBRICATING COMPOSITION FOR MUCOSA OR EPIDERMIS

[75] Inventors: Fumio Kasahara, Chiba; Kazuo Takeshita, Fujisawa, both of Japan

[73] Assignees: Kimitsu Chemical Laboratory Co. Ltd.; Showa Yakuhinkako Kabushiki Kaisha, both of Japan

[22] Filed: Feb. 11, 1974

[21] Appl. No.: 441,503

Related U.S. Application Data

[63] Continuation-in-part of Ser. No. 209,733, Dec. 20, 1971, abandoned.

[30] Foreign Application Priority Data

Dec. 21, 1970 Japan.............................. 45-114920

[52] U.S. Cl................................. 424/180; 424/195
[51] Int. Cl.²......................................... A61K 31/70
[58] Field of Search.................................... 424/180

[56] References Cited
FOREIGN PATENTS OR APPLICATIONS
34,485    1/1970    Japan................................. 424/180

OTHER PUBLICATIONS

*Chemical Abstracts* vol. 57, 749b, 1963; vol. 57, 7623d, (1962); vol. 74, 75199, (1971); vol. 75, 121401p.

*Primary Examiner*—Frederick E. Waddell

[57] ABSTRACT

This invention relates to a lubricating composition for mucosa and hypodermis, which is composed mainly of an alginic acid salt and fucoidin and produced from a sea weed belonging to phaeophyceae, and to a process for the preparation thereof.

4 Claims, 3 Drawing Figures

FIG. I

LUBRICATING COMPOSITION FOR MUCOSA OR EPIDERMIS

CROSS-REFERENCE TO RELATED APPLICATION

This application is a continuation-in-part of our co-pending application Ser. No. 209,733, filed Dec. 20, 1971, now abandoned.

BACKGROUND OF THE INVENTION:

1. Field of the Invention

This invention relates to a process for preparing from an alga belonging to phaephyceae a thready, mucous composition which comprises as main ingredients an alginic acid salt and fucoidin, and to its use as a lubricant. Especially, it relates to a mucous lubricating composition useful for facilitating parturition in animals.

A fetus of an animal, for example, a cow, is enveloped doubly with amnion and chorioid. Inside the amnion, there is contained amniotic fluid, and inside the chorioid there is contained urine. At the time of parturition, an embryonal sac covering the fetus if forced out with labor-pain, and a rupture of the chorioid firstly happens, whereby discharging the urine (the first rupture), and subsequently a rupture of the aminion, whereby discharging the amniotic fluid (the second rupture). The amniotic fluid is a specific high polymer solution which has a fluidity resembling that of albumen and is characterized by a high mucous and thready properties. It covers the fetus at the time of parturition, and performs the function of lubricating material to a birth canal, whereby facilitating the delivery of the fetus.

The amount of amniotic fluid is sufficient in the case of normal parturition, but in case the time for delivery is long or there is happened another trouble for delivery, the amount of amniotic fluid becomes insufficient, which results in difficult delivery. Further, as a result of recent high domestication (an increase of physique and insufficient exercise) of cattle, swine, and other domestic animals, the time required for parturition is likely to become long in these domestic animals, whereby bringing about undesired phenomena, such as damage to the birth canal and the fetus.

This invention has been accomplished as a result of investigation on the lubricating property of the amniotic fluid.

Therefore, the primary object of this invention is to provide the composition capable of giving lubrication to a birth canal as a substitute for the amniotic fluid and thus facilitating the delivery of the fetus.

2. Description of the Prior Art

There have been known several methods for preparing alginic acid or its alkali salts from the phaeophyceae. For instance, there have been known an "acid-neutralizing method" illustrated in the flow sheet of FIG. 1, and a "calcium method" illustrated in the flow sheet of FIG. 2.

However, there has not been known a method preparing an alginic acid salt and fucoidin coincidentally from the phaeophyceae nor use the products as a lubricant for the living bodies.

Figure 1:
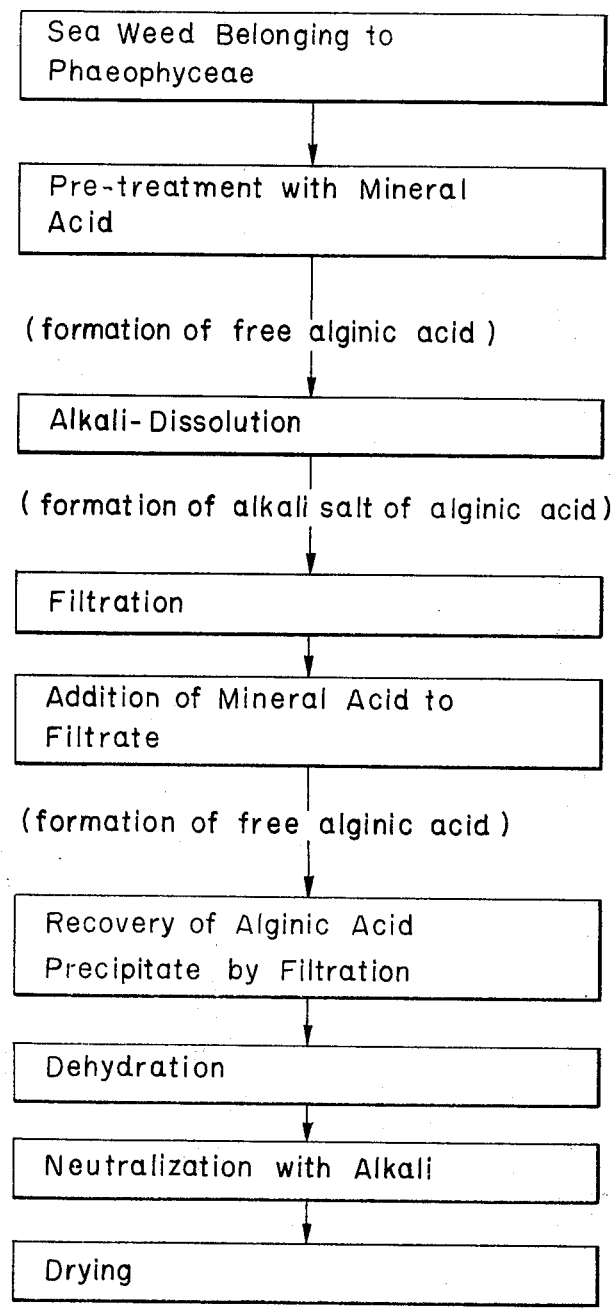
FIG. 1 is a flow sheet illustrating the well-known acid-neutralizing method preparing alginic acid or its alkali salt from the phaeophyceae.

DESCRIPTION OF THE INVENTION:

This invention relates to a mucous, thready composition having lubricating property, which is produced from the phaeophyceae such as sea tangle and ecklonia, and to a process for the preparation of such composition.

We have found that a lubricating agent composed solely of alginic acid salt is not suitable for delivery of the fetus in animals, and that the composition comprising alginic acid salt and fucoidin exhibits preferred properties for the lubricating agent.

It has been found that, based on our experimental works, it is essential to store a liquid between two frictional interfaces, namely the mucosa of the birth canal and a fur of the fetus, in order to attain a good lubrication at the time of parturition, and further substances having highly thready property, such as sodium polyacrylate, polyethylene oxide and potassium sodium polyphosphate, are preferable to afford lubrication for this purpose. It is considered that such substances having highly thready property are composed of the macromolecules, and are not likely to escape between the frictional interfaces of the animals. It has also been found that, when such substances is incorporated with a viscous substance having relatively low structural viscosity but showing liquid characteristic close to a Newtonian flow, such as alkali salt of alginic acid, fucoidin, gum arabic and carboxymethyl cellulose (C.M.C.), the resulting composition has a further improved lubrication. The reason is considered to be that such viscous substances forms synergistically a liquid film of much greater thickness, which is not likely escape between the two frictional interfaces, with the above-mentioned substances having thready property.

A composition comprising fucoidin as the viscous substance is especially preferred, because it is a natural substance, whereby will not cause any fear of side effects to the animals.

The alkali salts of alginic acid are also natural substances and make liquid having quite resembling Newtonial flow characteristics. Thus, use of the alkali salts of alginic acid are preferred.

We noticed that both fucoidin and the alginic acid salts are components contained in the phaeophyceae (such as sea tangle and ecklonia), and have studied a method for extracting them coincidentally from the phaeophyceae.

Fucoidin is a substance contained in cell-membrane of the phaeophyceae and is a metal salt of a polyglycosulfate composed mainly of fucose or grape sugar. Thus, fucoidin is a polymer comprising principally calcium salts of methyl pentose monosulfate and glucose monosulfate obtained from phaeophyceae. The calcium in fucoidin is organically combined so that it does not precipitate by adding barium chloride and cooling. Fucoidin is decomposed by acids. Fucoidin does not precipitate in the presence of calcium salts and is inactive to dilute alkali solution. It yields an insoluble salt by the reaction with trivalent metals and is sparingly soluble in organic solvents. Further, it is readily soluble in water, which makes it convenient to form a mucilaginous aqueous fucoidin solution.

Chemical properties of fucoidin are different from those of alginic acid or its salt in the following points:

1. To acids:

The alginic acid salts are converted to a water insoluble free acid in the presence of the acids, but the free acid is readily converted to the original salts by neutralization.

Fucoidin is decomposed with the acids. Even though the neutralization is effected on the decomposed product, viscosity and the other properties inherent to fucoidin cannot be restored.

2. To calcium salts:

In the presence of the calcium salts, alginic acid is converted to its water insoluble calcium salt and is precipitated.

Fucoidin is not influenced at all in the presence of the calcium salts, and does not form any precipitate.

3. To alkalis:

In the presence of the alkalis, alginic acid is converted to a water-soluble alkali salt of algic acid.

Fucoidin is not affected by dlute alkali.

Figure 2:
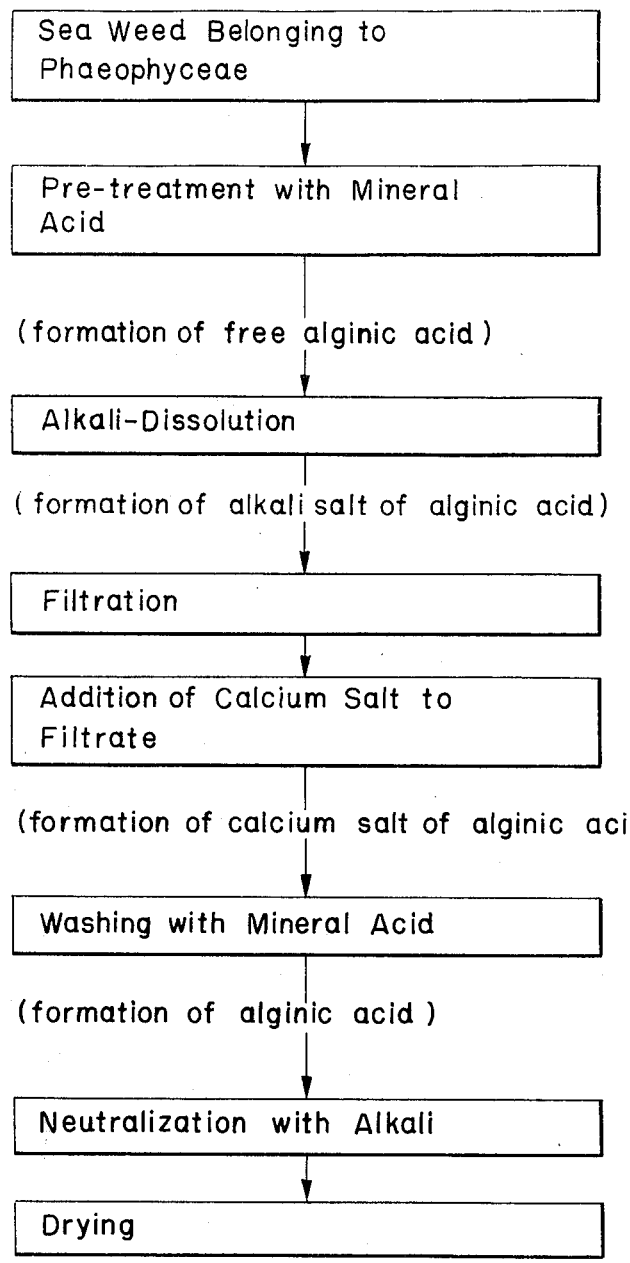
FIG. 2 is a flow sheet illustrating the well-known calcium method.

Because of the differences described above, fucoidin is not at all extracted by the conventional methods (see FIGS. 1 and 2) for preparing alginic acid or its alkali salt due to the decomposition of fucoidin.

We have now confirmed and discovered the following facts:

1. Fucoidin reacts with a trivalent metal such as Al and Fe to form an insoluble salt.

Alginic acid and its alkali salts react with such trivalent metal to form insoluble salts.

2. When a trivalent metal salt of fucoidin or alginic acid is washed with excessive caustic alkali in the hydrophilic organic solvents mixed with a suitable amount of water, such as 70% ethanol, 70% methanol and 60% isopropanol, the trivalent metal is eluted out by washing due to formation of a water-soluble complex salt, whereas fucoidin or arginic acid remains in the organic solvents by forming a precipitate.

3. The product which is obtained by substituting Ca included in fucoidin by the alkalis is water-soluble, and has the thready property.

We have succeeded in extracting alkali salt of alginic acid and fucoidin coincidentally from a kind of seaweed, i.e., the phaeophyceae by utilizing these characteristic of fucoidin and alginic acid or salt thereof.

Figure 3:
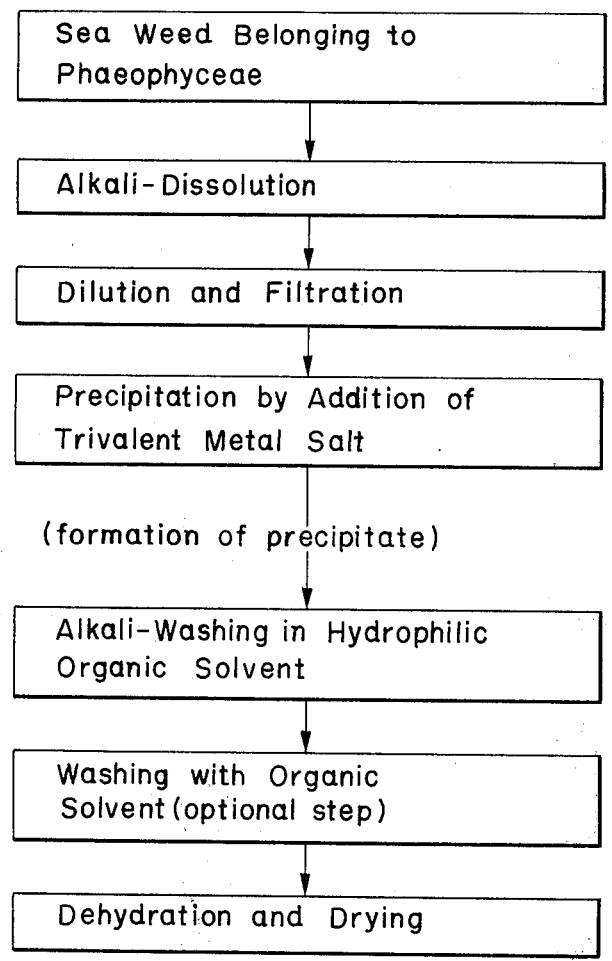
FIG. 3 is a flow sheet illustrating all steps for preparing the lubricating composition of this invention.

The steps for obtaining the composition of this invention will now be detailed by referring to FIG. 3.

First Step: Alkali Dissolution

In the conventional methods for preparing alginic acid, a treatment with mineral acid is conducted prior to the alkali dissolution. In this invention, however, the phaeophyceae is directly dissolved by an alkali without the acid treatment.

In sea weed, alginic acid is usually present in the form of calcium salt. Accordingly, it is preferred to use as a dissolving alkali an alkaline compound capable of readily forming an insoluble salt with calcium by double decomposition reaction, rather than caustic alkali. Suitable alkaline compounds are hydroxides, carbonates or phosphates of a monovalent metal or of magnesium, such as sodium or potassium carbonate, or sodium and potassium phosphates, e.g. $MH_2PO_4$, $M_2HPO_4$, $M_3PO_4$ (where M is sodium or potassium); or triphosphates, decaphosphates or hexaphosphates of sodium or potassium. It is also preferred to use an alkali having the function of softening and destroying the tissue of the sea weed. It has been confirmed by our experiments that use of a mixture comprising sodium pyrophosphate and/or sodium carbonate gives especially good results.

Suitably, from about 2 to about 20, preferably about 10, Kg of phaeophyceae are blended with 50 liters of water containing from 0.5 to 6 Kg of alkaline compound to effect the alkali-dissolving treatment. The alkali-dissolving treatment is carried out at 30°–80°C, preferably 50°–65°C, and generally for 2–4 hours.

Second Step: Dilution and Filtration

The paste-like liquor resulting from the first step is then diluted according to a customary method until the concentration calculated as alginic acid becomes 0.5 – 0.3%, and the resulting dilution is filtered by a conventional method. Since the thready property of fucoidin is readily lost under mechanical shearing force, it is necessary to avoid high pressure filtration. It is also necessary to avoid the use of a pump having a structure utilizing a violent shearing force in transportation of liquid.

Third Step: Precipitation

A salt of the trivalent metal, such as an aluminum salt or ferric salt, is added to the filtrate from the second step so as to precipiate trivalent metal salts of fucoidin and alginic acid.

As the trivalent metal salt to be added to the filtrate from the second step, there may be preferably used hydrochlorides, sulfates, acetates and alum group. The trivalent metal salt is used in an amount sufficient to precipitate fucoidin and the alginic acid salt, such as from about 10 to about 30 weight per cent of the trivalent metal salt, based on the weight of the phaeophyceae charged to the alkali-dissolving treatment.

At this precipitating step, the pH is adjusted to 6.5 – 9.0, preferably 7.0 – 7.8. When the precipitation medium is too acidic, fucoidin will be destroyed, and when the medium is too alkaline, the precipitation becomes insufficient.

Fourth Step: Alkali-Washing in Solvent

The precipitate from the third step is washed with caustic alkali in the hydrophilic organic solvent mixed with a suitable amount of water. Preferable examples of the hydrophilic organic solvent are methanol, ethanol and isopropanol. It is essential that the solvent concentration should be such that the resulting trivalent metal complex salt will be readily eluted out and removed by washing but fucoidin and the alkali salts of alginic acid will not be eluted out at all. In general, the solvent/water admixture will contain from about 40 to about 90% by weight of organic solvent with the balance being water. It has experimentally been found that the preferable solvent concentrations are about 50–85% in the case of methanol, about 45–80% in the case of ethanol, and about 45–75% in the case of isopropanol, respectively, with the balance being water. The concentration of alkali is from 0.5 to 2% by weight based on the mixtures of each solvent and water.

Fifth Step: Organic Solvent-Washing

In order to remove a remained caustic alkali component, a precipitate from the fourth step is washed 2 – 3 times with a hydrophilic organic solvent. It is possible to omit this step or to substitute this step by a step of neutralizing the excessive alkali with a weak acid.

Sixth Step: Dehydration and Drying

Water is removed from the resulting precipitates, and it is dried to form a solid product consisting essentially of a mixture of fucoidin and alginic acid salt in the weight ratio of alginic acid salt to fucoidin being from 1.6:1 to 3.6:1. When this solid product is dissolved in water to form a 0.4 to 15%, by weight, aqueous solution, it gives a solution having excellent lubricating properties and exhibiting a thready property. If the concentration of the solid product is less than 0.4%, the aqueous solution does not show adequate effects due to an insufficient mucilaginous property. However, if the concentration is more than 15%, the aqueous solution is difficult to use due to too high a viscosity.

Accordingly, the solution can be used very conveniently as an agent for lubricating the birth canal at the time of parturition in cattle, swine and other animals. Further, it has been confirmed that attainment of similar effects in human bodies can also be fully expected.

In one of our clinical experiments made on pregnant women, the delivery of a fetus could be greatly facilitated with effects of preventing damages on a birth canal, reducing the pressure imposed on the head of a neonate and releasing the mother from labour pains, by injecting a 1% solution of a powdery product obtained in Example 1 given below in pasteurized water into the vagina just before parturition by means of a pasteurized injector. Further, no residual side effects were observed. Accordingly, it has been confirmed that the composition can be effectively applicable to the animals as well as the human bodies.

The composition of this invention may be used as a lubricant for mucosa or epidermis in the various animals. For instance, when a veterinary surgeon treats a big animal by inserting his arm into a rectum or vagina, the insertion can be much facilitated by applying the composition of this invention around the arm.

The composition of this invention may optionally be mixed with carboxymethyl cellulose (C.M.C.), sodium polyacrylate, potassium sodium polyphosphate, polyethylene oxide or the like.

In order to heighten the solubility of the composition of this invention, it is preferred at the time of application to blend it with glucose, lactose or the like, or to add a surfactant, a coating agent or the like to the composition of this invention.

It is also possible to mix an antiseptic, a curing medicine or the like into the composition of this invention.

This invention will now be illustrated by the following examples.

EXAMPLE 1

10 kg of ecklonia collected at Shirahama, Chiba-Prefecture, Japan was cut into squares of about 1 cm, and 1 kg of sodium tertiary phosphate, 1 kg of sodium pyrophosphate, 0.5 kg of sodium carbonate and 50 liters of water were added thereto. Then, the blend was heated at 50°C. and agitated for 2 hours. Thus there was formed a paste-like liquor. The liquor was diluted and filtered, and 20 liters of a 10% solution of aluminum chloride was gradually added to the filtrate. The resultant precipitate was subjected to the centrifugal separation to remove water therefrom. The precipitate was dipped in 20 liters of 75% methanol, followed by addition of 2 liters of 30% caustic soda. The agitation was conducted for 1 hour and the precipitate was recovered by filtration. This alkali-washing treatment was repeated twice. Then, the precipitate was washed with 75% methanol free of caustic soda.

The resultant precipitate was dried to obtain 1.6 kg of a yellowish brown massive product, which was determined to have the following composition:

| | |
|---|---|
| alginic acid salt | 61.8% |
| fucoidin | 22.2% |
| protein admixtures | 1.0% |
| water | 15.0% |

The above product was pulverized to a powdery product.

The so obtained powdery product was easily soluble in water, and its aqueous solution was excellent in threading property.

In order to test the properties of the product, a 1.5% aqueous solution of the product was prepared, which was a mucous liquid having a high threading property and exhibiting an excellent lubricating property. Good lubricating effects were observed when the above aqueous solution was injected into a birth canal of a cow at the time of parturition.

Also good results were obtained when a concentrated solution of the above product having a concentration of 5 – 10% was applied directly to a birth canal or fetus at the time of parturition in a cow.

EXAMPLE 2

10 kg of arthrothamnus collected at Nemuro, Hokkaido, Japan was cut into squares of about 10 cm, and 1.5 kg of sodium pyrophosphate, 1.5 kg of sodium tertiary phosphate and 50 liters of water were added thereto. The blend was heated at 60°C. and agitated for 1 hour to effect dissolution. The solution was diluted 10 times and filtered. 22 liters of a 10% solution of aluminum sulfate was gradually added to the filtrate, and the resultant precipitate was subjected to the centrifugal separation. Then, the precipitate was dipped in 20 liters of 65% isopropanol, followed by addition of 2 liters of 30% caustic soda. The agitation was conducted for 1 hour, and the precipitate was recovered by filtration. This alkali-washing was repeated twice. Then, the precipitate was washed in 20 liters of 75% methanol.

The resultant precipitate was dried to obtain 1.7 g of yellowish brown massive product, which was determined to have the following composition:

| | |
|---|---|
| alginic acid salt | 62.3% |
| fucoidin | 22.0% |
| protein admixtures | 1.1% |
| water | 14.6% |

The massive product was pulverized to obtain a powdery product.

The product was dissolved in water to prepare an aqueous solution having a concentration of 1.5%. This aqueous solution was very mucous and excellent in lubricating property. When the solution was used at the time of parturition of a cow, excellent lubricating effects were obtained.

EXAMPLE 3

10 kg of ecklonia maxima produced in South Africa was pulverized to about 20 mesh, and was incorporated with 1.0 kg of sodium carbonate, 1.5 kg of sodium tertiary phosphate, 1.5 kg of sodium pyrophosphate and 50 liters of warm water maintained at 30°C. The blend was allowed to stand still over-night, and heated at 80°C. for 2 hours under agitation. The resulting solution was diluted 15 times and filtered. 25 liters of a 10% solution of ferric chloride was gradually added to the filtrate. The resultant precipitate was recovered by the centrifugal separation, and then dipped in 25 liters of 75% methanol, followed by addition of 2.5 liters of 30% caustic soda. The agitation was carried out for 1 hour and the precipitate was recovered by filtration. This alkali-washing treatment was repeated twice. Then, the precipitate was washed with 20 liters of 75% methanol, and dried to obtain 1.9 kg of a faintly yellowish brown massive product, which was determined to have the following composition:

| | |
|---|---|
| alginic acid salt | 65.4% |
| fucoidin | 18.1% |
| protein admixtures | 1.9% |
| water | 13.6% |

The massive product was pulverized to form a powdery product.

When the powdery product was used at the time of parturition of a cow in the same manner as described in Example 1, very excellent lubricating effects were obtained.

EXAMPLE 4

10 kg of ecklonia collected at Miura Peninsula, Kanagawa-Prefecture, Japan were cut into squares of 2 cm, and 1 kg of sodium tertiary phosphate, 1 kg of sodium carbonate and 70 liters of water were added thereto. The blend was heated at 50°C. for 2 hours under agitation. The resulting paste-like liquor was diluted and filtered. Then, 25 liters of a 10% solution of potassium alum $(AlK(SO_4)_2 \cdot 12H_2O)$ was gradually added to the filtrate. The resulting precipitate was treated in the same manner as in Example 1 to obtain 1.8 kg of a massive product which was determined to have the following composition:

| | |
|---|---|
| alginic acid salt | 56.0% |
| fucoidin | 23.4% |
| protein admixtures | 4.6% |
| water | 16.3% |

EXAMPLE 5

A filtrate obtained by repeating the treatment of Example 3 was gradually incorporated with 25 liters of a 10% solution of ferric chloride, and the resulting precipitate was treated in the same manner as in Example 3 to obtain 1.9 kg of faintly yellowish brown massive product.

EXAMPLE 6

A filtrate obtained by repeating the treatment of Example 2 was gradually incorporated with 20 liters of a 10% solution of iron alum $(Fe(NH_4)(SO_4)_2 \cdot 12H_2O)$, and the resultant precipitate was treated in the same manner as in Example 2 to obtain 1.65 kg of a massive product.

EXAMPLE 7

10 kg of ecklonia produced at Onjuku, Chiba-Prefecture, Japan was cut into squares of about 1 cm and blended with 1 kg of sodium tertiary phosphate, 1 kg of sodium pyrophosphate, 0.5 kg of sodium carbonate and 50 liters of water. The blend was heated at 60°C. for 2 hours under agitation to obtain a paste-like liquor. The liquor was diluted and filtered. 20 liters of a 10% solution of ferric acetate was gradually added to the filtrate, and the resulting precipitate was subjected to the centrifugal separation to remove water therefrom. The recovered precipitate was dipped in 20 liters of 75% methanol, followed by addition of 2 liters of 30% caustic soda. The agitation was conducted for 1 hour and the precipitate was recovered by filtration. This alkali-washing treatment was repeated twice. The resultant precipitate was washed with 75% methanol free of caustic soda and dried to obtain 1.5 kg of a yellowish brown massive product, which was determined to have the following composition:

| | |
|---|---|
| alginic acid salt | 58.9% |
| fucoidin | 24.0% |
| protein admixtures | 0.8% |
| water | 16.3% |

The above massive product was pulverized into a powdery product. The product was formed into a 1.5% aqueous solution, which was a mucous liquor having a high lubricating property. When the solution was used at the time of parturition of a cow in the same manner as in Example 1, excellent lubricating effects were obtained.

EXAMPLE 8

The procedure of Example 1 was used, except that the seaweed and the alkali (used as raw materials in the first step) and the precipitation agents (used in the third step) were replaced by the following substance:

| | | |
|---|---|---|
| Raw material: | Ecklonia collected at Shirahama, Chiba Prefecture, Japan | 10 kg |
| Dissolving agent: | $Na_2HPO_4$ | 1.0 kg |
| | Sodium pyrophosphate | 1.0 kg |
| | Sodium carbonate | 0.5 kg |
| | Water | 50 liters |
| Precipitation agent: | 10% solution of aluminum chloride | 20 liters |

The product obtained was a yellow-brown mass. The yield was 1.2 kg.

The composition was as follows:

| | |
|---|---|
| alginic acid salt | 56.7% |
| fucoidin | 24.2% |
| protein admixture | 0.8% |
| water | 18.3% |

The product showed a lubricating effect similar to that of the product obtained by Example 1.

EXAMPLE 9

The procedure of Example 2 was used except that the seaweed and the alkali (used as the raw materials in the first step) and the precipitation agents (used in the third step) were replaced by the following substances:

| | | |
|---|---|---|
| Raw material: | arthrothamnus collected at Nemuro, Hokkaido, Japan | 10 kg |
| Dissolving agent: | $NaH_2PO_4$ | 1.3 kg |
| | Sodium pyrophosphate | 1.0 kg |
| | Potassium carbonate | 0.5 kg |
| | Water | 50 liters |
| Precipitation agent: | 10% solution of aluminum sulphate | 23 liters |

The product obtained was a yellow-brown mass obtained in a yield of 1.1 kg. The composition was as follows:

| | |
|---|---|
| alginic acid salt | 45.8% |
| fucoidin | 28.8% |
| protein admixture | 1.3% |
| water | 24.1% |

This product had a lubricating effect similar to that of the product obtained by Example 2.

EXAMPLE 10

The procedure of Example 3 was followed except that the seaweed and the alkali (used as the raw materials in the first step) and the precipitation agents (used in the third step) were replaced by the following substances:

| | | |
|---|---|---|
| Raw material: | Ecklonia maxima collected in South Africa | |
| Dissolving agent: | $K_3PO_4$ | 1.0 kg |
| | Sodium pyrophosphate | 1.3 kg |
| | Caustic soda | 0.3 kg |
| | Water | 50 liters |
| Precipitation agent: | 10% solution of ferric chloride | 25 liters |

The product obtained was a yellow-brown mass. The yield was 1.9 kg. The composition was found as follows:

| | |
|---|---|
| alginic acid salt | 61.2% |
| fucoidin | 23.9% |
| protein admixture | 4.0% |
| water | 10.9% |

The product showed a lubricating effect similar to that of the product obtained in Example 3.

EXAMPLE 11

Following the procedure of Example 8, the following substances were used:

| | | |
|---|---|---|
| Raw material: | Ecklonia collected at Miura Peninsula, Kanagawa Prefecture, Japan | 10 kg |
| Dissolving agent: | $K_2HPO_4$ | 1.3 kg |
| | Potassium triphosphate | 1.0 kg |
| | Sodium carbonate | 1.0 kg |
| | Water | 50 liters |
| Precipitation agent: | 10% solution of potassium alum [Al K(SO$_4$)$_4$ . 12H$_2$O] | 25 liters |

The product obtained with a yield of 1.3 kg was a yellow-brown mass having the following composition:

| | |
|---|---|
| alginic acid salt | 52.7% |
| fucoidin | 25.6% |
| protein admixture | 5.2% |
| water | 16.5% |

The product showed a lubricating effect similar to that of the product obtained in Example 1.

EXAMPLE 12

Following the procedure of Example 10, the following substances were used:

| | | |
|---|---|---|
| Raw material: | Ecklonia maxima collected in South Africa | 10 kg |
| Dissolving agent: | $KHPO_4$ | 1.5 kg |
| | Sodium decaphosphate | 1.2 kg |
| | Sodium carbonate | 1.0 kg |
| | water | 50 liters |
| Precipitation agent: | 10% solution of ferric chloride | 25 liters |

The product obtained with yield of 1.2 kg was a yellow-brown mass having the following composition:

| | |
|---|---|
| alginic acid salt | 48.5% |
| fucoidin | 26.5% |
| protein admixture | 2.8% |
| water | 22.2% |

This product showed a lubricating effect which is similar to that of the product obtained in Example 3.

EXAMPLE 13

Following the procedure of Example 9, the following substances were used:

| | | |
|---|---|---|
| Raw material: | arthrothamnus collected at Nemuro, Hokkaido, Japan | 10 kg |
| Dissolving agent: | $K_3PO_4$ | 1.0 kg |
| | Sodium hexaphosphate | 1.2 kg |
| | Potassium carbonate | 1.0 kg |
| | Water | 50 liters |
| Precipitation agent: | 10% solution of ammonium ferric sulfate [NH$_4$ . Fe(SO$_4$)$_2$ . 12H$_2$O] | 20 liters |

The product obtained with yield of 1.15 kg was a yellow-brown mass having the following composition:

| | |
|---|---|
| alginic acid salt | 64.1% |
| fucoidin | 18.1% |
| protein admixture | 1.0% |
| water | 16.8% |

This product showed a lubricating effect similar to that of the product obtained in Example 2.

EXAMPLE 14

Following the procedure of Example 8, the following substances were used:

| | | |
|---|---|---|
| Raw material: | Ecklonia collected at Onjuku, Chiba Prefecture, Japan | 10 kg |
| Dissolving agent: | $Na_3PO_4$ | 1.0 kg |
| | Potassium decaphosphate | 1.2 kg |
| | Potassium carbonate | 1.0 kg |
| | Water | 50 liters |
| Precipitation agent: | 10% solution of iron acetate | 20 liters |

The product obtained with yield of 1.3 kg was a yellow-brown mass having the following composition:

| | |
|---|---|
| alginic acid salt | 57.6% |
| fucoidin | 19.9% |
| protein admixture | 2.2% |
| water | 20.2% |

This product showed a lubricating effect which was similar to that of the product obtained in Example 1.

What is claimed is:

1. A composition which in aqueous solution forms a mucosal or epidermal lubricant, said composition consisting essentially of a mixture of fucoidin and alginic acid salt in a weight ratio of alginic acid salt to fucoidin of from 1.6:1 to 3.6:1, said fucoidin being obtained from phaephyceae and comprisng principally calcium salts of methyl pentose monosulfate and glucose monosulfate, said fucoidin being decomposed by acid, being capable of remaining in aqueous solution in the presence of calcium salts, being inert to dilute alkali, forming an insoluble salt upon reaction with a trivalent metal, forming a mucilageneous squeous solution and being sparingly soluble in methanol, ethanol and propanol.

2. A process for the preparation of a composition having fucoidin and an alginic acid salt as its major components, comprising dissolving phaeophyceae in an alkaline aqueous solution containing at least one alkaline compound selected from the group consisting of hydroxides, carbonates and phosphates of monovalent metals and magnesium, filtering the resulting solution, adding at least one salt of a trivalent metal selected from the group consisting of iron and aluminum to the filtrate in an amount sufficient to precipitate fucoidin and trivalent metal salt of alginic acid, washing the resulting precipitate with a mixture of a hydrophilic organic solvent selected from the group consisting of methanol, ethanol and propanol and water containing at least one member selected from the group consisting of caustic soda, caustic potassium and ammonia, in an amount of from 0.5 to 2%, by weight, based on the weight of said solvent and water, to form a water-soluble trivalent metal complex salt and to remove the water-soluble complex salt from the precipitate, and drying the obtained precipitate, said precipitate having fucoidin and alginic acid salt as its major components, the weight ratio of alginic acid salt to fucoidin being 1.6:1 to 3.6:1.

3. The process according to claim 2, wherein said alkaline compound is a hydroxide, carbonate or phosphate of sodium or potassium.

4. A lubricant comprisijg a 0.4 to 15%, by weight, solution of the composition of claim 1.

* * * * *